US008367042B2

(12) United States Patent
Kim et al.

(10) Patent No.: US 8,367,042 B2
(45) Date of Patent: Feb. 5, 2013

(54) NANOPARTICLES OF LIGHT EMISSIVE POLYMERS AND PREPARATION METHOD THEREOF

(75) Inventors: Sehoon Kim, Seoul (KR); Ick Chan Kwon, Seoul (KR); Kwangmeyung Kim, Seoul (KR); Kuiwon Choi, Seoul (KR); Chang-Keun Lim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 594 days.

(21) Appl. No.: 12/576,193

(22) Filed: Oct. 8, 2009

(65) Prior Publication Data

US 2010/0290999 A1 Nov. 18, 2010

(30) Foreign Application Priority Data

May 13, 2009 (KR) .................. 10-2009-0041898

(51) Int. Cl.
*A61B 5/00* (2006.01)
(52) U.S. Cl. ........................................................ 424/9.6
(58) Field of Classification Search .................. None
See application file for complete search history.

(56) References Cited

U.S. PATENT DOCUMENTS

| 7,181,266 | B2 | 2/2007 | Frangioni et al. |
| 7,229,837 | B2 | 6/2007 | Chen |
| 2007/0069197 | A1 | 3/2007 | Leclerc |

FOREIGN PATENT DOCUMENTS

| EP | 0 707 021 | 4/1996 |
| JP | 2001-299676 | 10/2001 |
| JP | 2004-269439 | 9/2004 |
| WO | WO-2004/108902 | 12/2004 |
| WO | WO-2008/048190 | 4/2008 |
| WO | WO 2009107859 A2 * | 9/2009 |

OTHER PUBLICATIONS

Synthesis and characterization of new poly(cyanoterephthalylidene)s for light-emitting diodes, Synthetic Metals, 2001, 122, 401-408.*
Tuning of Redox Behavior and Fluorescence of Cyano-containing Oligophenylenevinylenes, MRS Proceedings, 1999.*
Derfus et al., Nano Letters (2004) 4(1):11-18.
Eggeling et al., Anal. Chem. (1998) 70:2651-2659.
Gao et al., Nature Biotechnology (2004) 22(8):969-976.
Greenham et al., Chemical Physiscs Letters (1995) 241:89-96.
Greenham et al., Nature (1993) 365:628-630.
Kim et al., Prog. Polym. Sci. (2007) 32:1031-1053.
Michalet et al., Science (2005) 307:538-544.
Resch-Genger et al., Nature Methods (2008) 5(9):763-775.
Seydack, Biosensors and Bioelectronics (2005) 20:2454-2469.
Wu et al., ACS Nano (2008) 2(11):2415-2423.
Zhang et al., Nature Reviews (2002) 3:906-918.
Debord et al., "Synthese de systemes macromoleculaires a doubles liaisons conjuguees," Bulletin de la Societe Chimique de France (1971) 4:1393-1401.
European Search Report for EP 09012987.5, mailed May 10, 2011, 9 pages.
Hoerhold et al., "Poly-(Arylen-Zyanoaethylene)—Untersuchung ueber den Einfluss der Struktur auf die Optisshen und Elektrophysikalischen Eigenschaften," Plaste und Kautschuk (1970) 17(2):84-88.
Jorgensen et al., "Valence band edges and optical band gaps of alternating substituted poly(phenylenevinylenes)," Polymer Bulletin (2003) 51(1):23-30.
Kim et al., "Conjugated polymer nanoparticles for biomedical in vivo imaging," Chemical Communications (2010) 46(10):1617-1619.
Lee et al., "Optical properties of segmented cyano-containing PPV-based chromophore for fluorescent sensing," Optical Materials (2003) 21(1-3):429-432.
Liu et al., "Conjugated polymers containing phenothiazine moieties in the main chain," Polymers for Advanced Technologies (2006) 17(6):468-476.
Liao et al., "Ruthenium-Catalyzed Knoevenagel Condensation: A New Route toward Cyano-Substituted Poly(p-phenylenevinylene)s," Macromolecules (2004) 37(8):7061-7063.
Park et al., "Synthesis and luminescence of new conjugated polymer," Polymer Preprints (1995) 36(1):375-376.
Pinto et al., "Light-emitting copolymers of cyano-containing PPV-based chromophores and a flexible spacer," Polymer (2000) 41(7):2603-2611.

* cited by examiner

*Primary Examiner* — Paul Dickinson
(74) *Attorney, Agent, or Firm* — Morrison & Foerster LLP

(57) ABSTRACT

Disclosed are nanoparticles of a light emissive polymer, comprising nanoparticles of a cyano-substituted poly(arylene vinylene) polymer; and a biocompatible surfactant adsorbed to the surface of the nanoparticles of the polymer, and preparation method thereof, wherein the method comprises: (1) uniformly mixing a dialdehyde monomer represented by a general formula OHC—$Ar_1$—CHO, a dicyanide monomer represented by a general formula NC—$Ar_2$—CN, and a liquid surfactant; (2) adding water to the resulting mixture to prepare an aqueous micelle dispersion; and (3) adding a polymerization catalyst to the aqueous micelle dispersion, followed by carrying out colloidal polymerization of the resulting mixture at room temperature under an atmosphere. The nanoparticles of the light emissive polymer of the invention are stabilized with a biocompatible surfactant, so that it can form a stable aqueous dispersion phase, and has particle size and fluorescence efficiency suitable for a biomolecular marker or a cell or in vivo imaging; therefore, it can be used as a cell or in vivo light emission contrast agent.

17 Claims, 6 Drawing Sheets

NANOPARTICLES OF LIGHT EMISSIVE POLYMERS AND PREPARATION METHOD THEREOF

CROSS-REFERENCE TO RELATED APPLICATIONS

This application claims benefit of Korean application No. 10-2009-0041898 filed 13 May 2009. The contents of the above patent application is incorporated by reference herein in its entirety.

BACKGROUND OF THE INVENTION

1. Field of the Invention

The present invention relates to nanoparticles of light emissive polymers and preparation method thereof. More particularly, the present invention relates to nanoparticles of light emissive polymers, having a particle diameter, emission performance and aqueous dispersion phase which are suitable for the application as a biomolecular marker, or applications to cells or in vivo applications, so that can be used as an optical imaging contrast agent, and preparation method thereof.

2. Description of the Prior Art

In life science, fluorescence-based techniques have been widely applied for defining various basic life phenomena from molecular biology to disease diagnosis. In particular, the fluorescence-based technique uses various experimental parameters including wavelength of excitation light, wavelength of fluorescence, fluorescence lifetime or fluorescence anisotropy, as well as fluorescence intensity, thereby making it possible to multiplex signals from a plurality of targets, and provides a resolution in nanometer level and sensitivity in single molecule level.

Fluorescence-related photophysical phenomena are sensitive to the change in surrounding environments, and there are various molecular-controllable phenomena such as extinction or increase of fluorescence, generation of energy transfer, etc. resulting from interactions between homogeneous or heterogeneous materials. Such properties have been employed for the development of intelligent contrast agents for the study of interactions between biomolecules, and early diagnosis of diseases.

Fluorescent materials which have been used as an immunomarker, or a contrast agent for cells or a living body include organic fluorescent molecules [D1: Kim et al., *Prog. Polym. Sci.* 32:1031-1053 (2007)], fluorescent proteins [D2: Zhang et al., *Nat. Rev. Mol. Cell. Bio.* 3:906-918 (2002)], and inorganic quantum dots [D3: Seydack et al., *Biosens. Bioelectron.* 20:2454-2469 (2005), D4: Gao et al., *Nat. Biotechnol.* 22:969-976 (2004), and D5: Michalet et al., *Science* 307:538-544 (2005)].

The performances of fluorescence-based molecule detection and imaging depend on optical properties of fluorescent marking materials or contrast agents, in particular, fluorescence intensity and optical stability. The fluorescence intensity defining the sensitivity limitation of signal detection is determined by the product of the fluorescence efficiency and the absorption coefficient of a fluorescent material. In particular, the absorption coefficient for excitation light should be high in order to apply the fluorescent material to cells or a living body, where the density of excitation light is low due to scattering or absorption of the light and autofluorescence interference is severe.

The absorption coefficient for excitation light of organic fluorescent molecules or nanoparticles containing organic fluorescent molecules depends on the chemical structure of the molecule. The organic fluorescent molecules such as fluorescein, rhodamine, cyanine, etc., as described in [D6: Resch-Genger et al., *Nat. Method* 5:763-775 (2008)], have a molar absorption coefficient ($\epsilon$) of from $2.5 \times 10^4$ to $2.5 \times 10^5$ $M^{-1}cm^{-1}$, which is not sufficient for clinical applications. In addition, organic fluorescent molecules such as coumarin, rhodamine, and the like have considerably low optical stability under continuous irradiation of excitation light, as described in Eggeling et al., *Anal. Chem.* 70:2651-2659 (1998) (D7).

Meanwhile, as described in D4, 5, and 6, inorganic quantum dots such as CdS, CdSe, CdTe, InP, PbS, etc. have a molar absorption coefficient ($\epsilon$) of from $5 \times 10^5$ to $5 \times 10^6$ $M^{-1}cm^{-1}$, which corresponds to scores of times the value of organic fluorescent molecules, and are optically stable. However, as described in Derfus et al., *Nano Lett.* 4:11-18 (2004) (D8), there is a limitation in application to cells or in vivo application due to potential toxicity problems caused by a heavy metal composition.

In addition, *ACS Nano* 2:2415-2423 (2008) (D9) discloses π-conjugated polymers having an absorption coefficient ($\epsilon$) of $1 \times 10^9$ $M^{-1}cm^{-1}$ or higher in a state of nanoparticle with a diameter of about 15 nm, and improved optical stability of $10^3$ times or more compared with organic fluorescent dyes under continuous excitation light irradiation. However, π-conjugated polymers such as poly[2-methoxy-5-(2-ethylhexyloxy)-1,4-phenylenevinylene](MEH-PPV), poly[2,5-di(3,7-dimethyloctyl)phenylene-1,4-ethynylene](PPE), poly[{9,9-dioctyl-2,7-divinylene-fluorenylene}-alt-co-{2-methoxy-5-(2-ethylhexyloxy)-1,4-phenylene}](PFPV), poly[(9,9-dioctylfluorenyl-2,7-diyl)-co-(1,4-benzo{2,1',3}-thiadiazole)](PFBT), etc., exhibit higher fluorescence efficiencies ($\Phi$)) in a solution, while the fluorescence efficiencies are in general significantly declined in solid phase such as nanoparticles, thin films or the like.

Furthermore, GREENHAM et al., *Nature* 365:628-630 (1993) (D10) and GREENHAM et al., *Chem. Phys. Lett.* 241:89-96 (1995) (D11) disclosed a cyano-substituted poly(phenylene vinylene)s. These materials are π-conjugated polymers having a cyanovinylene group in their structures, which have been reported to exhibit fluorescence efficiency ($\Phi$)) of 0.35 or higher in solid thin film. However, D10 and D11 use the π-conjugated polymers having a cyanovinylene group only for making thin films for electronic devices, and do not suggest using the same as a biomolecular marker, or optical image contrast agents to be injected into cells or a living body.

SUMMARY OF THE INVENTION

Therefore, in order to address the above matters, the various features described herein have been conceived.

An object of the present invention is to provide nanoparticles of light emissive polymers which can be used as a pure organic substance-based light emissive contrast agent for cells or a living body, having a particle diameter, emission performance and aqueous dispersion phase which are suitable for an application as a biomolecular marker, or applications to cells or a living body, and exhibiting a remarkably improved fluorescence intensity compared with the prior art organic fluorescent molecules or inorganic quantum dots currently used for in vivo fluorescence detection and imaging, while not containing any poisonous chemical elements to the living body, such as heavy metals or halogens, etc., and preparation method thereof.

The object of the present invention can be achieved by providing nanoparticles of light emissive polymers having the surface which is stabilized with a biocompatible surfactant, and having a particle diameter, emission performance and aqueous dispersion phase which are suitable for an application as a biomolecular marker, or applications to cells or a living body, and preparation method thereof.

Thus, the present invention provides nanoparticles of light emissive polymers, comprising: nanoparticles of a cyano-substituted poly(arylene vinylene) polymer represented by Formula 1 below; and a biocompatible surfactant adsorbed to the surface of the nanoparticles of the polymer of Formula 1 so as to stabilize the surface of the nanoparticles.

Formula 1:

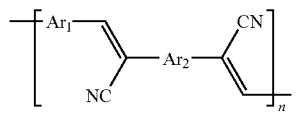

wherein n is an integer of 10 to 10,000; and $Ar_1$ and $Ar_2$ are an arylene group independently selected from the group consisting of phenylene, biphenylene, terphenylene, naphthalenylene, anthracenylene, fluorenylene, diphenylfluorenylene, carbazolylene, thiophenylene, puranylene, pyrrolylene, quinolinylene, quinoxalinylene, oxadiazolylene, diphenyloxadiazolylene, benzazolylene and benzdiazolylene which is unsubstituted or substituted with a linear or branched $C_{1-10}$ alkyl, alkoxy or thioalkoxy group.

The present invention also provides a preparation method of the nanoparticles of the light emissive polymers, comprising: (1) uniformly mixing a monomer represented by a general formula OHC—$Ar_1$—CHO ($Ar_1$ is an arylene selected from the group consisting of phenylene, fluorenylene and thienylene, which is unsubstituted or substituted with a linear or branched $C_{1-10}$ alkyl, alkoxy or thioalkoxy group), a monomer represented by the general formula NC—$Ar_2$—CN ($Ar_2$ is an arylene selected from the group consisting of phenylene, fluorenylene and thienylene, which is unsubstituted or substituted with a linear or branched $C_{1-10}$ alkyl, alkoxy or thioalkoxy group), and a liquid surfactant; (2) adding water to the resulting mixture to prepare an aqueous micelle dispersion; and (3) adding a polymerization catalyst to the resulting aqueous micelle dispersion, followed by carrying out colloidal polymerization at room temperature under an atmosphere.

The foregoing and other objects, features, aspects and advantages of the present invention will become more apparent from the following detailed description of the present invention when taken in conjunction with the accompanying drawings.

DETAILED DESCRIPTION OF THE INVENTION

Figure 1:
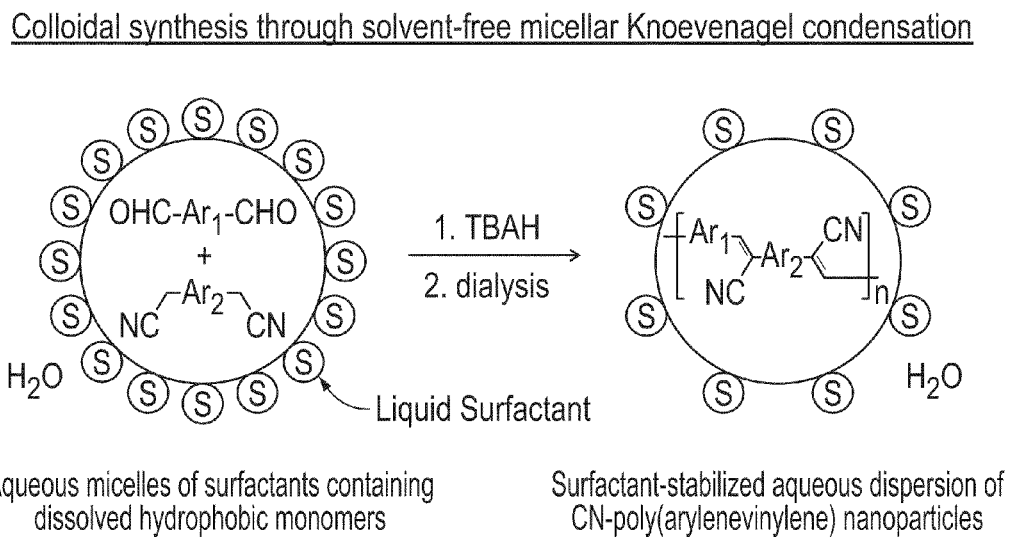
FIG. 1 is a schematic view of a preparation method of nanoparticles of a biocompatible conjugated polymer by a colloidal polymerization method according to the present invention.

In order to use nanoparticles of a light emissive polymer as a biomolecular marker, or an emissive contrast agent for imaging in cells or in vivo, the intensity of light emitted from the nanoparticles should meet the level for a clinical application, i.e., $10^2$ or $10^3$ times of the level of the prior art fluorescence contrast agents, for which the molar absorption coefficient ($\epsilon$) of the nanoparticles of the light emissive polymer for excitation light should be at least $1\times10^8$ $M^{-1}cm^{-1}$, the fluorescence efficiency ($\Phi$) should be at least 0.2, and a stable aqueous dispersion phase can be formed. The present invention provides nanoparticles of light emissive polymers that meet all requirements above.

Thus, the present invention relates to nanoparticles of light emissive polymers, comprising: nanoparticles of cyano-substituted poly(arylene vinylene) polymers represented by Formula 1 below; and a biocompatible surfactant adsorbed to the surface of the nanoparticles of the polymer of Formula 1.

Formula 1:

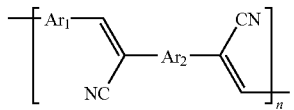

wherein n is an integer of 10 to 10,000; and $Ar_1$ and $Ar_2$ are an arylene group independently selected from the group consisting of phenylene, biphenylene, terphenylene, naphthalenylene, anthracenylene, fluorenylene, diphenylfluorenylene, carbazolylene, thiophenylene, puranylene, pyrrolylene, quinolinylene, quinoxalinylene, oxadiazolylene, diphenyloxadiazolylene, benzazolylene and benzdiazolylene which is unsubstituted or substituted with a linear or branched $C_{1-10}$ alkyl, alkoxy or thioalkoxy group.

In the present invention, the ratio between the cyano-substituted poly(arylene vinylene) polymer of Formula 1 and the biocompatible surfactant is in the range of from 1:7 to 1:12 by weight.

The nanoparticles of the light emissive polymer according to the present invention have a diameter of from 5 nm to 500 nm, which is suitable for the incorporation into cells and in vivo circulation.

The nanoparticles of the light emissive polymer according to the present invention have an absorption wavelength in the range of from 300 nm to 800 nm, which is suitable for the transmission to the tissues of a living body.

After irradiation of an excitation light, the wavelength of light emitted from the nanoparticles of the light emissive polymer ranges from 400 nm to 900 nm, which belongs to visible and near infrared regions.

When the nanoparticles according to the present invention are applied for an in vivo fluorescence imaging, the wavelength of the emitted light preferably ranges from 600 nm to 900 nm. If the wavelength of the emitted light is shorter than 600 nm, it overlaps with wavelengths of fluorescence (autofluorescence) emitted from fluorescent materials inherently present in the living body, which results in making it difficult to detect with a high sensitivity. In the meantime, if the wavelength of the emitted light is longer than 900 nm, it is difficult to obtain high emission efficiency, and in particular, it is disadvantageous because interference resulting from the absorption of the excessive amount of water present in the body increases.

The biocompatible surfactant is, preferably, a liquid surfactant. The surfactant provides the nanoparticles of the light emissive polymer with dispersion stability and biocompatibility in the environments inside the living body. Examples of the suitable surfactant include, but not limited thereto, surfactants of Tween group (e.g., Tween® 20, Tween® 60, Tween® 80, etc., available from Croda International PLC), Triton group (e.g., Triton® X-100 etc., available from Dow Chemical Company), Span group (e.g., Span® 20, Span9r® 60, Span® 80 etc., available from Croda International PLC).

Hereinafter, a preparation method of the nanoparticles of the light emissive polymer according to the present invention is described in detail.

The preparation method of the nanoparticles of the light emissive polymer according to the present invention employs a colloidal polymerization, wherein monomers are polymerized in an aqueous dispersion of uniform micelles formed by a biocompatible surfactant, with simultaneous formation of nanoparticles of a polymer, so as to prepare the desired nanoparticles of the light emissive polymer, having a diameter of from 5 nm to 500 nm and surface stabilized with the biocompatible surfactant, in an eco- and bio-friendly manner, without using an organic solvent harmful to a human body.

FIG. 1 illustrates a preparation process of the nanoparticles of the light emissive polymer according to the present invention.

In step (1), a dialdehyde monomer represented by the general formula OHC—Ar$_1$—CHO, a dicyanide monomer represented by the general formula NC—Ar$_2$—CN, and a liquid surfactant are uniformly mixed. The dialdehyde monomer and the dicyanide monomer are used in a molar ratio of 1:1, and the liquid surfactant is used by 20 to 100 times by weight of the total weight of the monomers.

In step (1), since the liquid surfactant can uniformly dissolve the hydrophobic polymerization monomers used as monomers, i.e., the dialdehyde monomer and the dicyanide monomer, there is no need to use any solvent in preparing the nanoparticles of the light emissive polymer in the present invention.

In step (2), water, preferably, deionized water, is added to the mixture obtained in step (1) to form an aqueous micelle dispersion. It is preferred to use deionized water because it is possible to minimize the influence of ions and impurities in forming nanoparticles.

In step (3), a polymerization catalyst is added, and colloidal polymerization is carried out at room temperature under an atmosphere, to form nanoparticles of a light emissive polymer with the surface to which a biocompatible surfactant is adsorbed. The polymerization catalyst may include tetraalkylammonium hydroxide, for example, tetrabutylammonium hydroxide (TBAH), tetramethylammonium hydroxide, tetraethylammonium hydroxide, or the like.

The preparation method of the nanoparticles of the light emissive polymer of the present invention may further comprise dialysis of the nanoparticles of the light emissive polymer obtained in step (3) for removing excessive amount of surfactant, catalyst and non-reacted monomers, so as to collect the nanoparticles of the light emissive polymer with surface stabilized by the biocompatible surfactant adsorbed thereon.

In the present invention, $Ar_1$ and $Ar_2$ of the emissive polymer of Formula 1 are varied, by which the light absorption and wavelength range of light emitted from the emissive polymers can be adjusted to correspond to visible and near infrared regions.

Figure 2A:
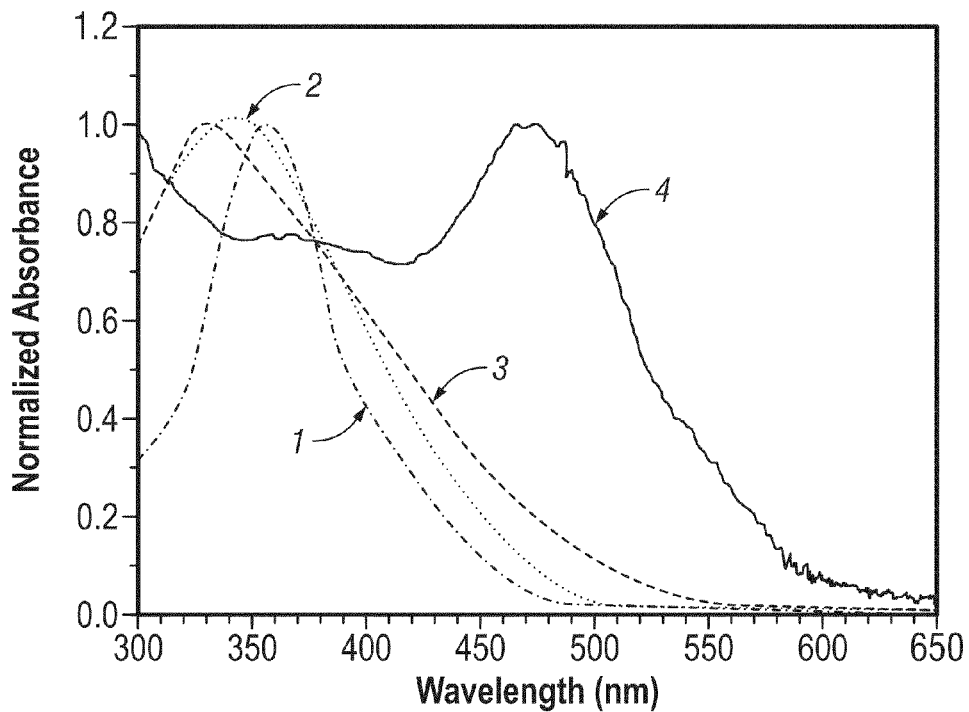
FIGS. 2a and 2b show absorption spectra (FIG. 2a) and fluorescence spectra (FIG. 2b) of nanoparticles of the light emissive polymers (1) CN-PFPV, (2) CN-PBPV, (3) CN-PPV and (4) CN-DOPPV according to the present invention.
Figure 2B:
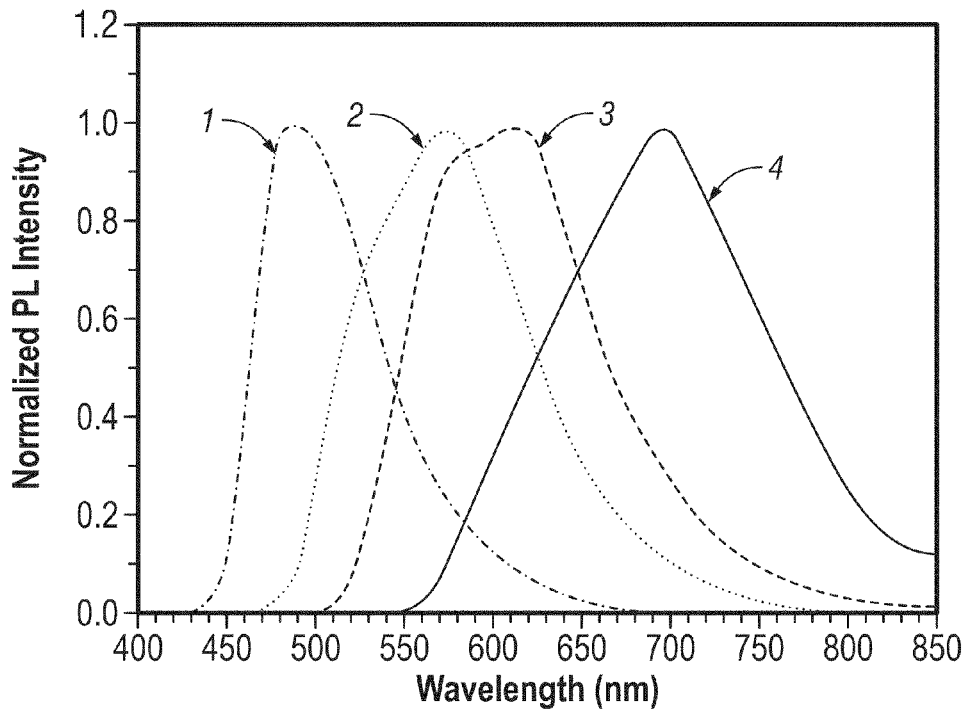

FIGS. 2a and 2b demonstrate that the present invention varies aromatic structures of the monomers, thereby preparing nanoparticles of a light emissive polymer having an absorption wavelength of 350 nm to 600 nm (See FIG. 2a) and a fluorescence wavelength of 450 nm to 800 nm (See FIG. 2b), while having a narrow diameter distribution in the range of from 5 nm to 300 nm measured by a dynamic light scattering method. In FIGS. 2a and 2b, lines (1) to (4) indicate the emissive polymer nanoparticles of the present invention wherein $Ar_2$ is phenylene, and $Ar_1$ is one selected from the groups represented by the following Formula 2:*

Formula 2:

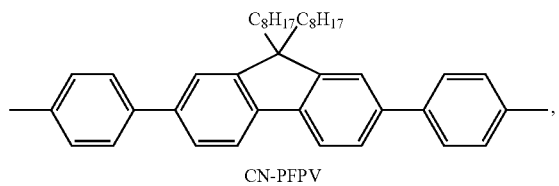

CN-PFPV

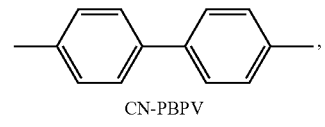

CN-PBPV

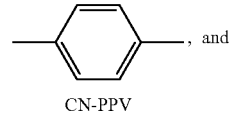

, and

CN-PPV

-continued

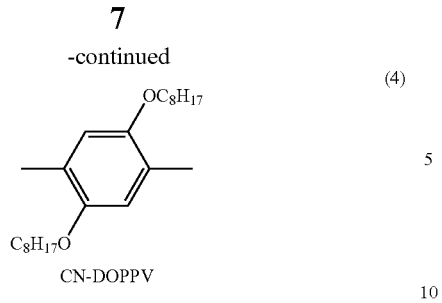

(4)

CN-DOPPV

Figure 3:
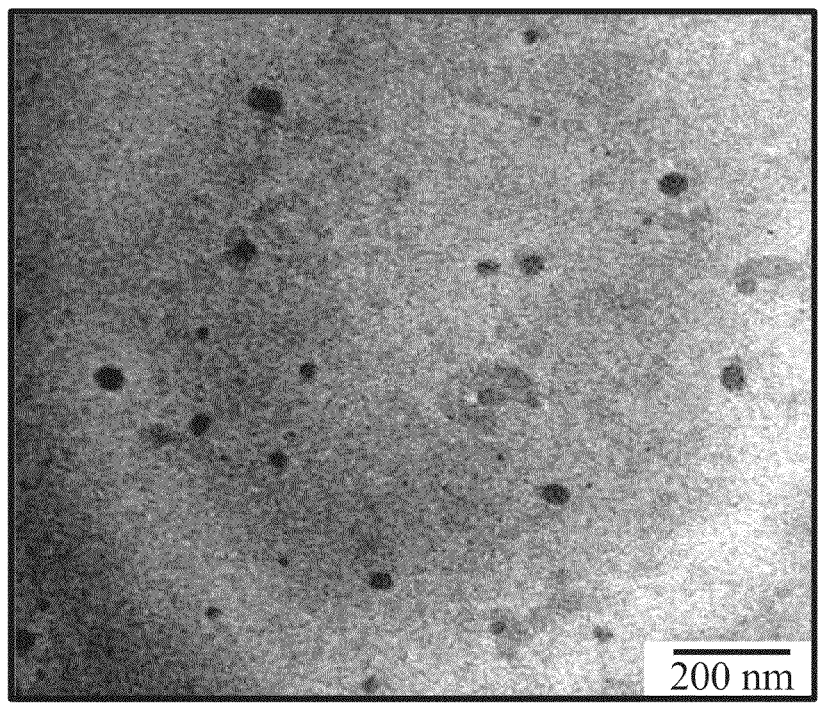
FIG. 3 is a transmission electron microscope photograph of nanoparticles of a light emissive polymer (CN-DOPPV) prepared in Example 1 according to the present invention.

FIG. 3 is a transmission electron microscopic photograph of the nanoparticles of the light emissive polymer according to the present invention.

As shown in FIGS. 2 and 3, in the present invention, it is possible to prepare nanoparticles of light emissive polymers having various fluorescence wavelengths while having a constant particle size, which are characteristics of the present invention distinguished from the prior art inorganic quantum dots whose absorption and fluorescence wavelengths depend on their particle size.

Figure 5A:
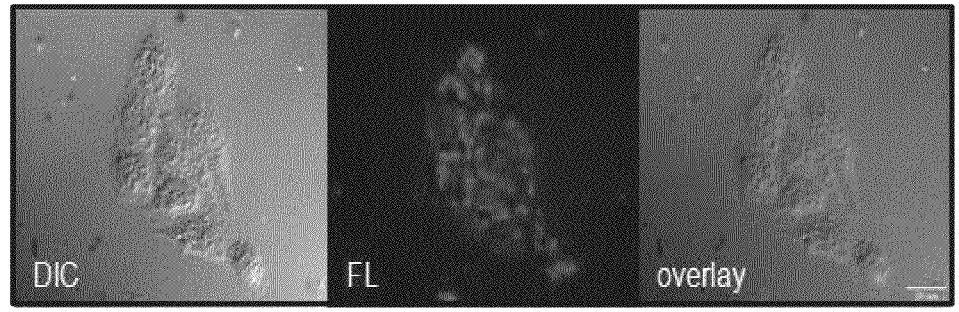
FIGS. 5a and 5b are optical photographic images of living cancer cells (HeLa cell) into which the nanoparticles of the light emissive polymer CN-DOPPV (FIG. 5a) and the CN-PPV (FIG. 5b) prepared in Example 1 according to the present invention were internalized, wherein "DIC" is a bright field image as a differential interference contrast image, "FL" is a fluorescence image, and "overlay" is an image obtained by overlapping DIC and FL.
Figure 5B:
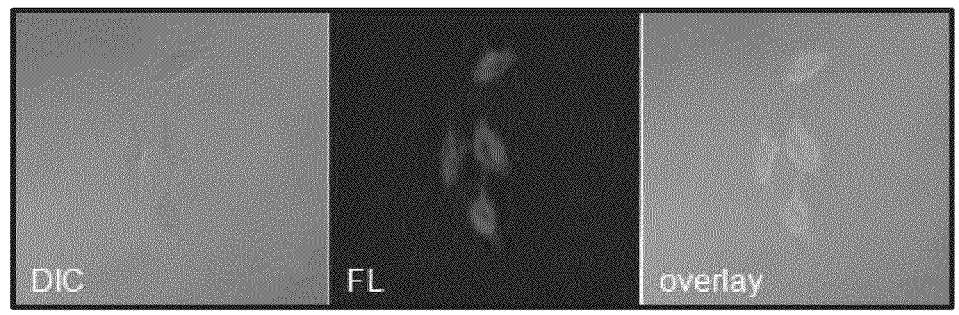
Figure 6:
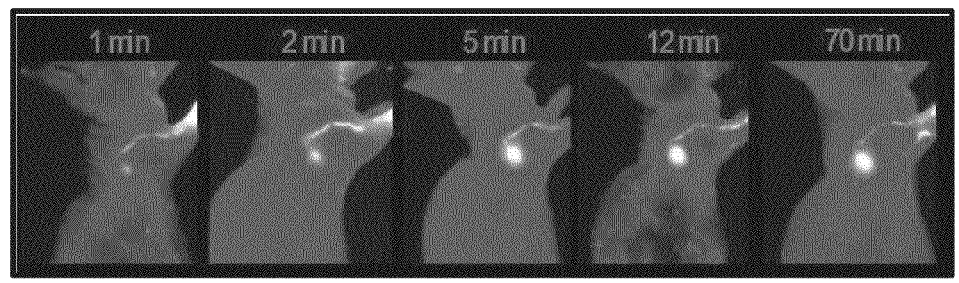
FIG. 6 is an in vivo near infrared fluorescence photographic image of sentinel lymph node mapping behavior on time when the nanoparticles of the light emissive polymer (CN-DOPPV) prepared in Example 1 according to the present invention was injected.

FIGS. 5 to 7 show the availability of the nanoparticles of the light emissive polymer according to the present invention as image contrast agents, which was confirmed through optical imaging experiments on cells and small animals. As shown in FIGS. 5 to 7, the nanoparticles of the light emissive polymer according to the present invention has a remarkably higher fluorescence intensity compared with the prior art fluorescence contrast agents, and a particle diameter which is suitable for cell imaging and sentinel lymph node mapping. In particular, compared with the prior art isotope tracers and blue dyes for detecting a sentinel lymph node, the nanoparticles of the light emissive polymer according to the present invention rapidly arrive in lymph node and stay there for a sufficient time period. Thus, if the nanoparticles of the light emissive polymer according to the present invention are used together with a simple fluorescence detector as proposed in JP 2001-299676 A, JP 2004-269439 A and U.S. Pat. No. 7,181,266 B2, even a person who is not a skilled person can quickly, accurately and easily detect sentinel lymph node, so that the nanoparticles of the light emissive polymer according to the present invention can be practically used in a cancer surgery, sentinel lymph node biopsy (SLNB). In addition, unlike the conventional lymphoscintigraphy, the nanoparticles of the light emissive polymer according to the present invention do not include radiation, can be easily handled, and do not require large facilities for sentinel lymph node biopsy, which allow using the nanoparticles of the light emissive polymer for a tumor removal operation via a sentinel lymph node biopsy even in a small hospital.

EXAMPLES

The examples of the present invention will now be described in detail, which are merely illustrative, not to limit the present invention thereto.

Example 1

Preparation of Light Emissive Polymer Nanoparticles (1) Preparation of cyano-substituted poly [{2-dioctyloxy-1,4-divinylene-phenylene}-alt-co-{1,4-phenylene}](CN-DOPPV) Nanoparticles The nanoparticles of polymer (CN-DOPPV) of Formula 1, wherein $Ar_1$ is phenylene substituted with two octyloxy groups, and $Ar_2$ is phenylene, whose surface is stabilized with a surfactant, was prepared according to the method illustrated in FIG. 1. Its detailed preparation procedure is as follows:

25.8 mg of 2,5-bis(octyloxy)terephthalaldehyde (Adrich) and 10.3 mg of p-xylylene dicyanide (TCI) were added to 1 g of Tween® 80 (commercially available from Sigma Co.), the resulting mixture was heated with hot air so as to make uniformly dissolved, and then allowed to cool down to room temperature. 5 mL of deionized water (Milli-Q, 18.2 MΩcm) was added to 0.3 g of the resulting solution to form a clear aqueous micelle dispersion solution. 0.2 mL of 1.0 M tetrabutylammonium hydroxide (TBAH) in methanol (Aldrich) was added to the aqueous micelle dispersion solution, and colloidal polymerization was carried out at room temperature under an atmosphere. After 12 hours, the reaction solution was purified by dialysis (cellulose ester, MW cutoff=300 kDa) with deionized water for two days, to obtain 6.7 g of aqueous dispersion of CN-DOPPV nanoparticles whose surface are stabilized with Tween® 80.

In order to determine the composition of the aqueous dispersion of CN-DOPPV nanoparticles, the total weight of CN-DOPPV nanoparticles aqueous dispersion obtained after lyophilizing 3 mL of reaction solution and the weight of pure CN-DOPPV nanoparticles after removing the surfactant Tween® by washing with ethanol were respectively measured. As a result, it was found that 4.1 mg (polymerization yield 89%) of pure CN-DOPPV nanoparticles without surfactant was stabilized with excessive amount of Tween® 80 (40.4 mg).

(2) Preparation of nanoparticles of cyano-substituted poly[{9,9-dioctyl-2,7-diphenyl-difluorene-4',4"-diyl}-alt-co-{1,4-divinylene-phenylene}](CN-PFPV), cyano-substituted poly[{4,4'-divinylene-biphenylene}-alt-co-{1,4-phenylene}] (CN-PBPV) and cyano-substituted poly(1,4-phenylene vinylene) (CN-PPV)

CN-PFPV, CN-PBPV and CN-PPV nanoparticles were prepared respectively using 4,4'-(9,9-dioctyl-9H-fluorene-2,7-diyl)dibenzaldehyde and p-xylyrene dicyanide, 4,4'-biphenyldicarboxaldehyde and p-xylyrene dicyanide, and terephthalaldehyde and p-xylyrene dicyanide as monomers in the same manner as described in (1) of Example 1.

Example 2

Figure 4:
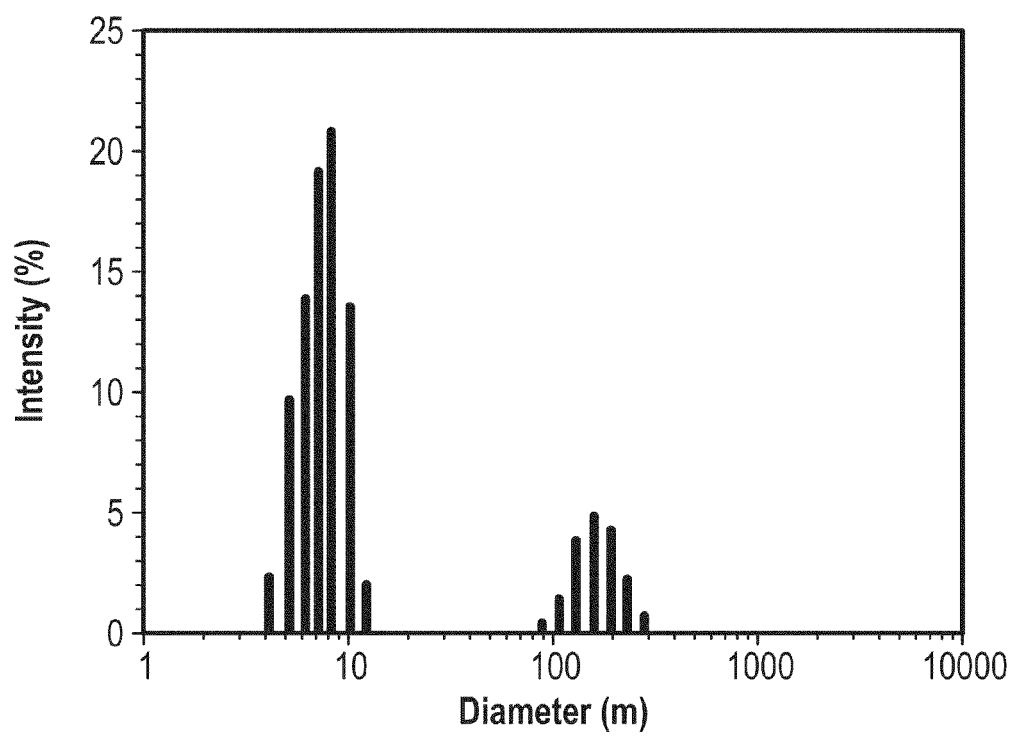
FIG. 4 illustrates a particle diameter distribution in an aqueous dispersion of the nanoparticles of the light emissive polymer (CN-DOPPV) prepared in Example 1 according to the present invention, determined with a dynamic light scattering method.

Evaluation of Characteristics of Light Emissive Polymer Nanoparticles (1) Evaluation of Particle Characteristics of Light Emissive Polymer Nanoparticles The shape and size of CN-DOPPV nanoparticles whose surface was stabilized with a surfactant, which was prepared in (1) of Example 1, were observed with transmission electron microscope (CM30, FEI/Philips, 200 kV), and the results are illustrated in FIG. 3. In addition, the particle size distribution in an aqueous dispersion phase was determined by a dynamic light scattering method (BI-9000 AT digital autocorrelator, Brookhaven), and its results are shown in FIG. 4. The CN-DOPPV nanoparticles consist of spherical particles with an average diameter of about 34 nm as shown in FIG. 3, and their average diameter in an aqueous dispersion was 59±5 nm as shown in FIG. 4.

(2) Evaluation of Optical Characteristics of Light Emissive Polymer Nanoparticles The aqueous dispersion of CN-DOPPV nanoparticles prepared in (1) of Example 1 was diluted by 20 times with deionized water, absorption and fluorescence spectra were then determined with UV-vis. spectrometer (Agilent 8453) and fluorescence spectrophotometer (Hitachi F-7000), results of which are illustrated in FIGS. 2a and 2b. The curved lines indicated as (4) in FIGS. 2a and 2b are results of optical characteristics for aqueous dispersion of CN-DOPPV nanoparticles. A relative fluorescence efficiency of CN-DOPPV nanoparticles calculated based on an ethanol solution of rhodamine B was 0.25. Accordingly, it was found that the nanoparticles of the light emissive polymer prepared in Example 1 of the present invention has fluorescence efficiency, which is suitable to be used as a biomolecular marker, or a light emitting contrast agent for imaging inside cells and in vivo imaging.

Optical characteristics of CN-PFPV, CN-PBPV and CN-PPV nanoparticles were evaluated in the same manner as for the CN-DOPPV nanoparticles, and the results are also provided in FIGS. 2a and 2b. In FIGS. 2a and 2b, lines (1), (2) and (3) are for CN-PFPV, CN-PBPV and CN-PPV, respectively.

Example 3

Observation of In Vivo Fluorescence of Light Emissive Polymer Nanoparticles

Figure 2C:
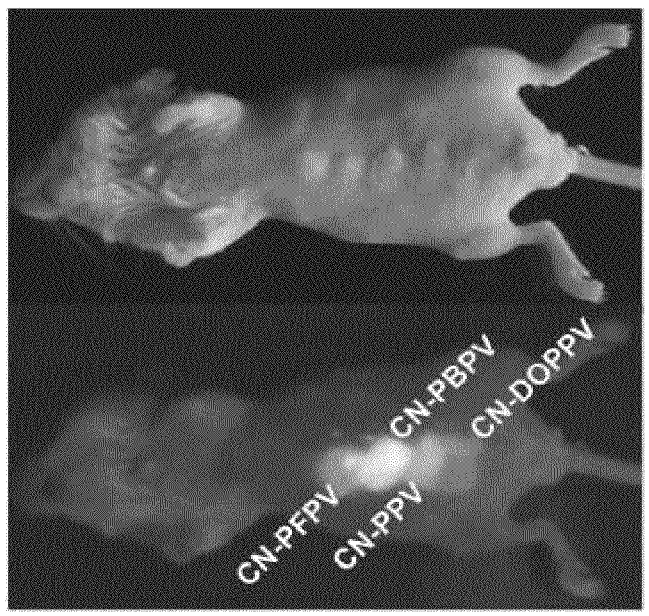
FIG. 2c is a fluorescence color photograph observed with naked eyes outside the body of an experimental mouse under a 365 nm ultraviolet lamp after each of aqueous dispersions of four types of nanoparticles above was subcutaneously injected to mice.

Each 50 ml μL of the aqueous dispersions of CN-DOPPV, CN-PFPV, CN-PBPV and CN-PPV nanoparticles prepared in Example 1 was subcutaneously injected into experimental mice, to which 365 nm of handheld ultraviolet lamp having a radiance of 1-2 $mW/cm^2$ was irradiated. A fluorescence photographic image observed with naked eyes is presented in FIG. 2c. FIG. 2c shows that intense fluorescence color was observed from the injected nanoparticle spots of the light emissive polymer of the present invention.

Example 4

Cell Imaging and Fluorescence Detection of Sentinel Lymph Nodes with Light Emissive Polymer Nanoparticles (1) Cell Imaging Each 100 μL of aqueous dispersions of CN-DOPPV and CN-PPV nanoparticles prepared in Examples 1 and 2 was put into a living cancer cell (HeLa cells) culture medium, which was then incorporated into the cell for three hours. An optical image of the nanoparticle-incorporated cells was observed with a fluorescence microscope (AppliedPrecision equipped with a 60× oil lens, Olympus). The results are provided in FIGS. 5a and 5b, which show that intense fluorescence of CN-DOPPV (FIG. 5a) and CN-PPV (FIG. 5b) nanoparticles was observed in cytoplasm of the cancer cells.

(2) In Vivo Near Infrared Fluorescence Imaging of Sentinel Lymph Node

FIGS. 2a and 2b show that CN-DOPPV nanoparticles prepared in Example 1 exhibit intense fluorescence in the near infrared region of 700 nm or higher which is suitable for in vivo fluorescence imaging. Thus, immediately after 10 μl of CN-DOPPV aqueous dispersion was subcutaneously injected into the forepaw pad of a peritoneal-anesthetized male mouse (BALB/c, the age of five weeks, Institute of Medical Science, Tokyo), a near infrared fluorescence image as shown in FIG. 6 was obtained under 535 nm light irradiation using an imaging device (Kodak Image Station 400MM) equipped with a near infrared region optical filter (e700WA). Immediately after the injection, the movement of CN-DOPPV nanoparticles flowing along the lymphatic vessel was traced by fluorescence image outside the body. As shown in FIG. 6, CN-DOPPV nanoparticles quickly reached the axillery sentinel lymph node within one minute, and a very intensive and vivid sentinel lymph node image was obtained in high quality within five minutes. The CN-DOPPV nanoparticles remained at the sentinel lymph node for more than 70 minutes, and no flow to a downstream lymph node was observed.

Figure 7A:
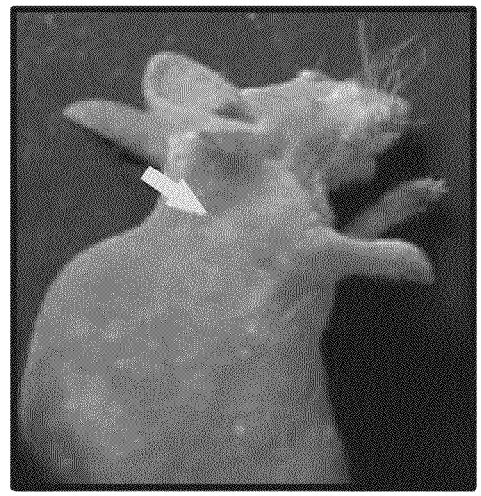
FIGS. 7a and 7b are fluorescence color photographic images of sentinel lymph node observed under a 365 nm ultraviolet lamp with naked eyes outside the body (FIG. 7a) and during surgery (FIG. 7b), after the nanoparticles of the light emissive polymer (CN-DOPPV) prepared in Example 1 according to the present invention was injected.
Figure 7B:
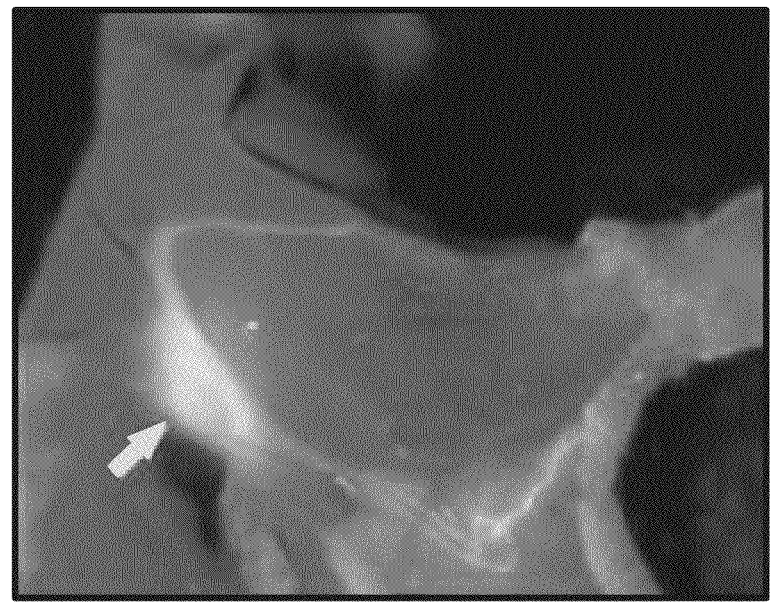

(3) Fluorescence Color Imaging of Sentinel Lymph Node Outside the Body and After Detachment of Epidermis After the completion of the experiment of (2) in Example 4, fluorescence color photographic images as shown in FIGS. 7a and 7b were taken with a general digital camera under a 365 nm portable ultraviolet lamp having an irradiation of 1-2 $mW/cm^2$. FIG. 7a is a photograph taken outside the body, and FIG. 7b is a photograph taken after detachment of epidermis. FIGS. 7a and 7b show that the CN-DOPPV nanoparticles have high fluorescence intensity, so that the nanoparticle-accumulated sentinel lymph node can be observed with naked eyes under a general handheld ultraviolet lamp, without special imaging equipment as used for the experiment of (2) in Example 4. After the epidermis was detached, more intense fluorescence was observed, thereby demonstrating that the sentinel lymph node can be specified quickly and accurately during operation.

As described above, the present invention provide nanoparticles of the light emissive polymer of the present invention having a particle diameter, emission performance and aqueous dispersion phase which are suitable for an application as a biomolecular marker, or to cells or a living body, being a pure organic substance containing neither halogen atom nor heavy metal, and exhibiting a remarkably improved fluorescence intensity compared with the prior art fluorescence contrast agents, and thus, can provide a fluorescence image with a small amount of injection.

In addition, in the present invention, the nanoparticles of the light emissive polymer can be prepared in an eco- and bio-friendly manner without using an organic solvent; therefore, the method of the present invention has no potential toxic problem of the prior art inorganic quantum dots, and thus, it provides the possibility of the nanoparticles of the light emissive polymer for an actual clinic application. In the preparation method of the nanoparticles of the light emissive polymer by colloidal polymerization method, a final product is directly obtained through one-step polymerization reaction from monomers. Thus, the method of the present invention is simple and easy compared with the prior art method, i.e., a precipitation method as described in D9, comprising dissolving light emissive polymer obtained by a solution polymerization in an organic solvent, followed by precipitating the polymer in water with a diluted concentration, so as to obtain nanoparticles of the polymer. Further, the present invention provides the possibility of producing in a large scale a stable aqueous dispersion of nanoparticles in a higher concentration. In the precipitation method, it is not possible to prepare nanoparticles of light emissive polymers having a low solubility, because the polymers should be uniformly dissolved in an organic solvent before the precipitation process, whereas in the colloid polymerization method according to the present invention, there is no limitation regarding the solubility of the polymer to be obtained, because the nanoparticles are prepared in the form of a final product and it is not required any re-dissolving process in an organic solvent. Therefore, the colloidal polymerization method according to the present invention is advantageous in that nanoparticles of light emissive polymer even with a low solubility can be prepared, so far as the solubility of monomers in a liquid surfactant is secured.

What is claimed is:

1. Nanoparticles of a light emissive polymer, comprising nanoparticles of cyano-substituted poly(arylene vinylene) polymer represented by Formula 1 below; and a biocompatible liquid surfactant adsorbed to the surface of the nanoparticles of the polymer:

Formula 1:

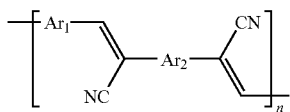

wherein n is an integer of 10 to 10,000, and
wherein $Ar_1$ is selected from the groups represented by Formula 2:

Formula 2:

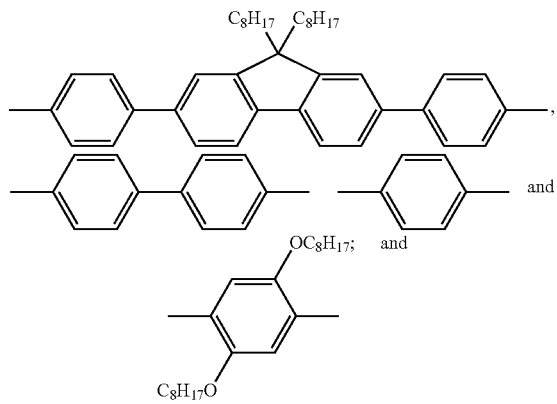

wherein $Ar_2$ is phenylene.

2. The nanoparticles according to claim 1, wherein a ratio between the nanoparticles of the cyano-substituted poly(arylene vinylene) polymer represented by Formula 1 and the biocompatible surfactant is 1:7 to 1:12 by weight.

3. The nanoparticles according to claim 1, wherein the surfactant is selected from the group consisting of Tween® 20, Tween® 60, Tween® 80, Triton® X-100, Span® 20, Span® 60 and Span® 80.

4. The nanoparticles according to claim 1, having a diameter in the range of from 5 nm to 500 nm.

5. The nanoparticles according to claim 1, having an absorption wavelength in the range of from 300 nm to 800 nm.

6. The nanoparticles according to claim 1, having a light emission wavelength in the range of from 400 nm to 900 nm.

7. The nanoparticles according to claim 6, having a light emitting wavelength of 450 nm or higher, and used as a fluorescence contrast agent for cell imaging.

8. The nanoparticles according to claim 6, having a light emission wavelength of 530 nm or higher, and used as a fluorescence contrast agent for in vivo imaging.

9. The nanoparticles according to claim 6, having a diameter of from 10 nm to 50 nm and a light emission wavelength of 600 nm or higher, and used as a contrast agent for fluorescence detection of sentinel lymph node.

10. A method to prepare the nanoparticles of claim 1, comprising:
(1) uniformly mixing a monomer of formula OHC—$Ar_1$—CHO, a monomer of formula NC—$Ar_2$—CN, and a liquid surfactant;
(2) adding water to the resulting mixture to prepare an aqueous micelle dispersion; and
(3) adding a polymerization catalyst to the aqueous micelle dispersion, followed by carrying out colloidal polymerization of the resulting mixture at room temperature under an atmosphere, to obtain the nanoparticles of the light emissive polymer, surface of which is stabilized with the surfactant.

11. The method according to claim 10, further comprising dialysis of the nanoparticles of the light emissive polymer obtained in step (3) for removing excessive amount of surfactant, catalyst and non-reacted monomers.

12. The method according to claim 10, wherein the monomer of formula OHC—$Ar_1$—CHO and the monomer of formula NC—$Ar_2$—CN are used in molar ratio of 1:1 in step (1), and the liquid surfactant used is 20 to 100 times by weight of the total weight of the monomers.

13. The method according to claim 10, wherein in step (1), the monomer of formula OHC—$Ar_1$—CHO and the monomer of formula NC—$Ar_2$—CN are uniformly dissolved in the liquid surfactant without an organic solvent.

14. The method according to claim 10 or 11, wherein the polymerization catalyst is selected from the group consisting of tetrabutylammonium hydroxide, tetramethylammonium hydroxide and tetraethylammonium hydroxide.

15. The method according to claim 10, wherein diameter of the nanoparticles of the light emissive polymer obtained in step (3) is in the range of from 5 nm to 500 nm.

16. The method according to claim 10, wherein an absorption wavelength of the nanoparticles of the light emissive polymer obtained in step (3) is in the range of from 300 nm to 800 nm.

17. The method according to claim 10, wherein a light emission wavelength of the nanoparticles of the light emissive polymer obtained in step (3) is in the range of from 400 nm to 900 nm.

* * * * *